(12) United States Patent
Wagner

(10) Patent No.: US 7,022,479 B2
(45) Date of Patent: *Apr. 4, 2006

(54) SENSITIVE, MULTIPLEXED DIAGNOSTIC ASSAYS FOR PROTEIN ANALYSIS

(75) Inventor: Richard W. Wagner, Concord, MA (US)

(73) Assignee: Compound Therapeutics, Inc., Waltham, MA (US)

( * ) Notice: Subject to any disclaimer, the term of this patent is extended or adjusted under 35 U.S.C. 154(b) by 543 days.

This patent is subject to a terminal disclaimer.

(21) Appl. No.: 10/212,620

(22) Filed: Aug. 5, 2002

(65) Prior Publication Data

US 2003/0032049 A1    Feb. 13, 2003

Related U.S. Application Data

(63) Continuation-in-part of application No. 09/755,663, filed on Jan. 4, 2001, now Pat. No. 6,489,116.

(60) Provisional application No. 60/177,873, filed on Jan. 24, 2000.

(51) Int. Cl.
| | |
|---|---|
| C12Q 1/68 | (2006.01) |
| C07H 21/02 | (2006.01) |
| C07H 21/04 | (2006.01) |
| C07K 14/00 | (2006.01) |

(52) U.S. Cl. .................. 435/6; 435/7.1; 530/350; 530/387.1; 536/23.1; 536/23.4; 536/24.33

(58) Field of Classification Search .................. 435/6, 435/29, 69.1, 68.1; 536/23.1, 23.4, 24.3, 536/24.33; 436/536, 518
See application file for complete search history.

(56) References Cited

U.S. PATENT DOCUMENTS

| | | | |
|---|---|---|---|
| 4,587,044 A | 5/1986 | Miller et al. | |
| 5,223,409 A | 6/1993 | Ladner et al. | |
| 5,264,563 A | 11/1993 | Huse | |
| 5,270,163 A | 12/1993 | Gold et al. | |
| 5,270,170 A | 12/1993 | Schatz et al. | |
| 5,424,186 A | 6/1995 | Fodor et al. | |
| 5,432,018 A | 7/1995 | Dower et al. | |
| 5,498,530 A | 3/1996 | Schatz et al. | |
| 5,541,061 A | 7/1996 | Fodor et al. | |
| 5,565,324 A | 10/1996 | Still et al. | |
| 5,605,793 A | 2/1997 | Stemmer | |
| 5,627,024 A | 5/1997 | Maruyama et al. | |
| 5,639,603 A | 6/1997 | Dower et al. | |
| 5,643,768 A | 7/1997 | Kawasaki | |
| 5,658,754 A | 8/1997 | Kawasaki | |
| 5,723,323 A | 3/1998 | Kauffman et al. | |
| 5,733,731 A | 3/1998 | Schatz et al. | |
| 5,751,629 A | 5/1998 | Nova et al. | |
| 5,770,455 A | 6/1998 | Cargill et al. | |
| 5,789,208 A | 8/1998 | Sharon | |
| 5,795,747 A | 8/1998 | Henco et al. | |
| 5,849,878 A | 12/1998 | Cantor et al. | |
| 5,965,133 A | 10/1999 | Cantor et al. | |
| 5,985,575 A | 11/1999 | Wickens et al. | |
| 6,258,558 B1 | 7/2001 | Szostak et al. | |
| 6,281,344 B1 | 8/2001 | Szostak et al. | |

FOREIGN PATENT DOCUMENTS

| | | |
|---|---|---|
| WO | WO 91/05058 | 4/1991 |
| WO | WO 92/00091 | 1/1992 |
| WO | WO 92/02536 | 2/1992 |
| WO | WO 92/18645 | 10/1992 |
| WO | WO 93/03172 | 2/1993 |
| WO | WO 95/11922 | 5/1995 |
| WO | WO 95/32425 | 11/1995 |
| WO | WO 96/22391 | 7/1996 |
| WO | WO 98/16636 | 4/1998 |
| WO | WO 98/58080 | 12/1998 |
| WO | WO 99/51773 | 10/1999 |
| WO | WO 00/09464 | 2/2000 |
| WO | WO- 00/32823 A1 | 6/2000 |
| WO | WO 00/34784 | 6/2000 |

OTHER PUBLICATIONS

Tillib, SV and Mirzabekov, AD. 2001. Advances in the analysis of DNA sequence variations using oligonucleotide microchip technology. Curr Opin Biotechnol. Feb.;12(1):53-8.*

Husimi et al., "Role of the Virus-Type Strategy in Encoded Molecular Evolution," Progress in Biophysics and Molecular Biology, vol. 65 (Suppl. 1), Abstract P-A5-04 (1996).

Niemeyer et al., "Hybridization Characteristics of Biomolecular Adaptors, Covalent DNA-Streptavidin Conjugates," *Bioconjugate Chem.* 9:168-175 (1998).

(Continued)

*Primary Examiner*—David Guzo
*Assistant Examiner*—Laura McGillem
(74) *Attorney, Agent, or Firm*—Ropes & Gray LLP, Fish & Neave IP Group

(57) ABSTRACT

Disclosed herein are methods for detecting multiple compounds in a sample, involving: (a) contacting the sample with a mixture of binding reagents, the binding reagents being nucleic acid-protein fusions, each having (i) a protein portion which is known to specifically bind to one of the compounds and (ii) a nucleic acid portion which encodes the protein portion and which includes a unique identification tag; (b) allowing the protein portions of the binding reagents and the compounds to form complexes; (c) capturing the binding reagent-compound complexes; (d) amplifying the nucleic acid portions of the complexed binding reagents; and (e) detecting the unique identification tag of each of the amplified nucleic acids, thereby detecting the corresponding compounds in the sample. Also disclosed herein are kits for carrying out such methods.

44 Claims, No Drawings

OTHER PUBLICATIONS

Niemeyer et al., "Oligonucleotide-Directed Self-Assembly of Proteins: Semisynthetic DNA—Streptavidin Hybrid Molecules as Connectors for the Generation of Macroscopic Arrays and the Construction of Supramolecular Bioconjugates," *Nucleic Acids Research* 22:5530-5539 (1994).

Niemeyer et al., "Self-Assembly of DNA-Streptavidin Nanostructures and Their Use as Reagents in Immuno-PCR," *Nucleic Acids Research* 27:4553-4561 (1999).

Niemeyer et al., "Functionalization of Covalent DNA-Streptavidin Conjugates by Means of Biotinylated Modulator Components," *Bioconjugate Chem.* 10:708-719 (1999).

Niemeyer et al., "DNA-Directed Immobilization: Efficient, Reversible, and Site-Selective Surface Binding of Proteins by Means of Covalent DNA-Streptavidin Conjugates," *Analytical Biochemistry* 268:54-63 (1999).

Niemeyer et al., "Evaluation of Single-Stranded Nucleic Acids as Carriers in the DNA-Directed Assembly of Macromolecules," Journal of Biomolecular Structure & Dynamics 17:527-538 (1999).

Abelson, "Directed Evolution of Nucleic Acids by Independent Replication and Selection," *Science* 249:488-489 (1990).

Barrett et al., "A Monoclonal Antibody Specific for a Dynorphin Precursor," *Neuropeptides* 6:113-120 (1985).

Botstein et al., "Strategies and Applications of in Vitro Mutagenesis," *Science* 229:1193-1201 (1985).

Bujard et al., "[26] A T5 Promoter-Based Transcription-Translation System for the Analysis of Proteins in Vitro and in Vivo," *Methods in Enzymology* 155:416-433 (1987).

Clackson et al., "In Vitro Selection from Protein and Peptide Libraries," *Tibtech* 12:173-184 (1994).

Cwirla et al., "Peptides on Phage: A Vast Library of Peptides for Identifying Ligands," *Proc. Natl. Acad. Sci.* 87:6378-6382 (1990).

Devlin et al., "Random Peptide Libraries: A Source of Specific Protein Binding Molecules," *Science* 249:404-406 (1990).

Eigen et al., "Molecular Quasi-Species," *Journal of Physical Chemistry* 92:6881-6891 (1988).

Eigen et al., "The Hypercycle. Coupling of RNA and Protein Biosynthesis in the Infection Cycle of an RNA Bacteriophage," *Biochemistry* 30:11005-11018 (1991).

Eigen, "Viral Quasispecies," *Scientific American* 269:32-39 (1993).

Eigen, "New Concepts for Dealing with the Evolution of Nucleic Acids," *Cold Spring Harb. Symp. Quant. Biol.* 52:307-320 (1987).

Eigen et al., "Evolutionary Molecular Engineering Based on RNA Replication," *Pure & Appl. Chem.* 56(8):967-978 (1984).

Gersuk et al., "High-Affinity Peptide Ligands to Prostate-Specific Antigen Identified by Polysome Selection," *Biochem. Biophys. Res. Commun.* 232(2):578-582 (1997).

Geysen et al., "Use of Peptide Synthesis to Probe Viral Antigens for Epitopes to a Resolution of a Single Amino Acid," *Proc. Natl. Acad. Sci.* 81:3998-4002 (1984).

Guatelli et al., "Isothermal, in vitro Amplification of Nucleic Acids by a Multienzyme Reaction Modeled after Retroviral Replication," *Proc. Natl. Acad. Sci.* 87:1874-1878 (1990).

Higuchi, "Using PCR to Engineer DNA," Stockton Press 61-70 (1989).

Horwitz et al., "Selection of New Biological Activities from Random Nucleotide Sequences: Evolutionary and Practical Considerations," *Genome* 31:112-117 (1989).

Hui et al., "Mutagenesis of the Three Bases Preceding the Start Codon of the B-galactosidase mRNA and its Effect on Translation in *Escherichia coli*," *The EMBO Journal* 3:623-629 (1984).

Hunkapiller et al., "A Microchemical Facility for the Analysis and Synthesis of Genes and Proteins," *Nature* 310:105-111 (1984).

Jamieson et al., "In Vitro Selection of Zinc Fingers with Altered DNA-Binding Specificity," *Biochemistry* 33:5689-5695 (1994).

Kraus et al., "Purification of Low-Abundance Messenger RNAs from Rat Liver by Polysome Immunoadsorption," *Proc. Natl. Acad. Sci.* 79:4015-4019 (1982).

Leung et al., "A Method for Random Mutagenesis of a defined DNA Segment using a Modified Polymerase Chain Reaction," *Technique* 1:11-15 (1989).

Lizardi et al., "Exponential Amplification of Recombinant-RNA Hybridization Probes," *Biotechnology* 6:1197-1202, (1988).

Matteucci et al., "Targeted Random Mutagenesis: The Use of Ambiguously Synthesized Oligonucleotides to Mutagenize Sequences Immediately 5' of an ATG Initiation Condon," *Nucleic Acids Research* 11:3113-3121, (1983).

Matthews et al., "Substrate Phage: Selection of Protease Substrates by Monovalent Phage Display," *Science* 260: 1113-1117 (1993).

Nemoto et al., "In vitro virus: Bonding of mRNA bearing puromycin at the 3'-terminal end to the C-terminal end of its encoded protein on the ribosome in vitro," *FEBS* 414:405-408 (1997).

Niemeyer et al., "Oligonucleotide-Derected Self-Assembly of Proteins: Semisynthetic DNA—Streptavidin Hybrid Molecules as Connectors for the Generation of Macroscopic Arrays and the Construction of Supramolecular Bioconjugates," Nucl. Acid Res. 22:5530-5539 (1994).

Nielsen et al., "Synthetic Methods for the Implementation of Encoded Combinatorial Chemistry," *J. Am. Chem. Soc.* 115:9812-9813 (1993).

Oehlenschlager et al., "30 Years Later—A New Approach to Sol Spiegelman's and Leslie Orgel's in vitro Evolutionary Studies. Dedicated to Leslie Orgel on the Occasion of his 70th birthday," *Orig Life Evol Biosph* 27:437-457 (1997).

Oldenburg et al., "Peptide Ligands for a Sugar-Binding Protein Isolated from a Random Peptide library," *Proc. Natl. Acad. Sci.* 89:5393-5397 (1992).

Peters et al., "N-terminal Amino Acid Sequences and C-terminal Residues of Rat Alpha-fetoprotein Electrophoretic Variants, 'Fast' and 'Slow'," *Scand. J. Immunol* 8:299-304 (1978).

Rebar et al., "Zinc Finger Phage: Affinity Selection of Fingers with New DNA-Binding Specificities," *Science* 263:671-673 (1994).

Sarkar et al., "Characterization of Polymerase Chain Reaction Amplification of Specific Alleles," *Analytical Biochemistry* 186:64-68 (1990).

Schatz, "Use of Peptide Libraries to Map the Substrate Specificity of a Peptide-Modifying Enzyme: A 13 Residue Consensus Peptide Specifies Biotinylation in *Escherichia coli*," *Bio/Technology* 11:1138-1143 (1993).

Scott et al., "Searching for Peptide Ligands with an Epitope Library," *Science* 249:386-390 (1990).

Scott et al., "A Family of Concanavalin A-Binding Peptides from a Hexapeptide Epitope Library," *Proc. Natl. Acad. Sci.* 89:5398-5402 (1992).

Wells et al., "Cassette Mutagenesis: An Efficient Method for Generation of Multiple Mutations at Defined Sites," *Gene* 34:315-323 (1985).

Bevan et al., "Identifying Small-Molecule Lead Compounds: The Screening Approach to Drug Discovery," TIBTECH 13:115-121 (1995).

Maclean et al., "Encoded Combinatorial Chemistry: Synthesis and Screening of a Library of Highly Functionalized Pyrrolidines," Proc. Natl. Acad. Sci. USA 94:2805-2810 (1997).

Kerr et al., "Encoded Combinatorial Peptide Libraries Containing Non-Natural Amino Acids," J. Am. Chem. Soc. 115:2529-2531 (1993).

Ohlmeyer et al., "Complex Synthetic Chemical Libraries Indexed with Molecular Tags," Proc. Natl. Acad. Sci. USA 90:10922-10926 (1993).

Chen et al., "Biased Combinatorial Libraries: Novel Ligands for the SH3 Domain of Phosphatidylinositol 3-Kinase," J. Am. Chem. Soc. 115:12591-12592 (1993).

Nicolaou et al., "Radiofrequency Encoded Combinatorial Chemistry," Angew. Chem. Int. Ed. Engl. 34:2289-2291 (1995).

Sebestyen et al., "Efficiency and Limitations of the Portioning-Mixing Peptide Synthesis," Peptides pp. 63-64 (1992).

Moran et al., "Radio Frequency Tag Encoded Combinatorial Library Method for the Discovery of Tripeptide-Substituted Cinnamic Acid Inhibitors of the Protein Tyrosine Phosphatase PTP1B," J. Am. Chem. Soc. 117:10787-10788 (1995).

Schena et al., "Quantitative Monitoring of Gene Expression Patterns with a Complementary DNA Microarray," Science 270:467-470 (1995).

Combs et al., "Protein Structure-Based Combinatorial Chemistry: Discovery of Non-Peptide Binding Elements to Src SH3 Domain," J. Am. Chem. Soc. 118:287-288 (1996).

Ellington and Szostak, Nature 346:818-822 (1990).

Ellington and Szostak, Nature 355:850-852 (1992).

Tuerk and Gold, Science 249:505-510 (1990).

Irvine et al., J. Mol. Biol. 222:739-761 (1991).

Oliphant et al., Mol. Cell Biol. 9:2944-2949 (1989).

Blackwell et al., Science 250:1104-1110 (1990).

Pollock and Treisman, Nuc. Acids Res. 18:6197-6204 (1990).

Thiesen and Bach, Nuc. Acids Res. 18:3203-3209 (1990).

Bartel et al., Cell 67:529-536 (1991).

Stormo and Yoshioka, Proc. Natl. Acad. Sci. USA 88:5699-5703 (1991).

Bock et al., Nature 355:564-566 (1992).

Green et al., Nature 347:406-408 (1990).

Robertson and Joyce, Nature 344:467-468 (1990).

Beudry and Joyce, Science 257:635-641 (1992).

Bartel and Szostak, Science 261:1411-1418 (1993).

Lorsch and Szostak, Nature 371:31-36 (1994).

Cuenoud and Szostak, Nature 375:611-614 (1995).

Chapman and Szostak, Chemistry and Biology 2:325-333 (1995).

Lohse and Szostak, Nature 381:442-444 (1996).

Ellman et al., Meth. Enzymol. 202:301-336 (1991).

Milstein, Sci. Amer. 243:66-74 (1980).

Smith, Science 228:1315-1317 (1985).

Parmley and Smith, Gene 73:305-318 (1988).

McCafferty et al., Nature 348:552-554 (1990).

Cull et al., Proc. Natl. Acad. Sci. USA 89:1865-1869 (1992).

Korman et al., Proc. Natl. Acad. Sci. USA 79:1844-1848 (1982).

Mattheakis et al., Proc. Natl. Acad. Sci. USA 91:9022-9026 (1994).

Mattheakis et al., Meth. Enzymol. 267:195-205 (1996).

Hanes and Pluckthun, Proc. Natl. Acad. Sci. USA 94:4937-4942 (1997).

Brenner and Lerner, Proc. Natl. Acad. Sci. USA 89:5381-5383 (1992).

Traut and Monro, J. Mol. Biol. 10:63-72 (1964).

Smith et al., J. Mol. Biol. 13:617-628 (1965).

Ekland et al., Nucl. Acids Research 23:3231-3238 (1995).

Stemmer, Nature 370: 389-391 (1994).

Krayevsky and Kukhanova, Progress in Nucleic Acids Research and Molecular Biology 23:1-51 (1979).

Needels et al., "Generation and Screening of an Oligonucleotide-Encoded Synthetic Peptide Library," Proc. Natl. Acad. Sci. USA 90:10700-10704 (1993).

* cited by examiner

SENSITIVE, MULTIPLEXED DIAGNOSTIC ASSAYS FOR PROTEIN ANALYSIS

CROSS REFERENCE TO RELATED APPLICATIONS

This application is a continuation-in-part of U.S. Ser. No. 09/755,663, filed Jan. 4, 2001 now U.S. Pat. No. 6,489,116, which claims the benefit of the filing date of provisional application, U.S. Ser. No. 60/177,873, filed Jan. 24, 2000, now abandoned.

BACKGROUND OF THE INVENTION

In general, the invention relates to diagnostic methods involving multiplex analysis.

A variety of methods exist to detect multiple species in a biological sample. These include ELISA based immunoabsorbent assays, protein biochips, and the like. Each of these methods suffers from limitations in detection sensitivity or selectivity, due, for example, to kinetics of binding or sensitivity of detection reagents. In addition, these techniques are also limited in terms of the number of molecules that can be rapidly detected.

SUMMARY OF THE INVENTION

The present invention involves a novel multiplex diagnostic approach for the ultra-sensitive detection of molecules in biological samples.

In general, in a first aspect, the invention features a method for detecting multiple different compounds in a sample, the method involving: (a) contacting the sample with a mixture of binding reagents, the binding reagents being nucleic acid-protein fusions, each having (i) a protein portion which is known to specifically bind to one of the compounds and (ii) a nucleic acid portion which includes a unique identification tag and which in one embodiment, encodes the protein; (b) allowing the protein portions of the binding reagents and the compounds to form complexes; (c) capturing the binding reagent-compound complexes; (d) amplifying the unique identification tags of the nucleic acid portions of the complexed binding reagents; and (e) detecting the unique identification tag of each of the amplified nucleic acids, thereby detecting the corresponding compounds in the sample.

In preferred embodiments, the sample is a biological sample; the nucleic acid-protein fusion is an RNA-protein fusion; the nucleic acid-protein fusion is covalently linked; the nucleic acid-protein fusion is covalently linked through a peptide acceptor; the peptide acceptor is puromycin; the binding reagents do not bind the compounds through compound-specific antibody domains; each of the binding reagents includes a scaffold domain; each of the binding reagents includes a fibronectin scaffold domain; the fibronectin scaffold domain is the 10$^{th}$ domain of fibronectin type III; each of the binding reagents includes an antibody scaffold domain; the binding reagents bind the compounds with equilibrium constants of less than about 500 nM; the unique identification tags are detected using a solid support to which are immobilized nucleic acids specific for the unique identification tags and the detection is accomplished by hybridization of the unique identification tags to the immobilized nucleic acids; the solid support is a chip; the immobilized nucleic acids are DNAs, preferably configured as a DNA array; the amplifying step (d) is carried out using quantitative PCR; the compounds are proteins; the mixture of binding reagents includes at least 5 different nucleic acid-protein fusions, each specifically binding to a different compound; the mixture of binding reagents includes at least 100 different nucleic acid-protein fusions, each specifically binding to a different compound; the mixture of binding reagents includes at least 40,000 different nucleic acid-protein fusions, each specifically binding to a different compound; and/or the mixture of binding reagents includes at least 500,000 different nucleic acid-protein fusions, each specifically binding to a different compound.

In a second aspect, the invention features a method for detecting a compound in a sample, the method involving: (a) contacting the sample with a binding reagent, the binding reagent being a nucleic acid-protein fusion having (i) a protein portion which is known to specifically bind to the compound and (ii) a nucleic acid portion which includes a unique identification tag and which, in one embodiment, encodes the protein; (b) allowing the protein portion of the binding reagent and the compound to form a complex; (c) capturing the binding reagent-compound complex; (d) amplifying the unique identification tag of the nucleic acid portion of the complexed binding reagent; and (e) detecting the unique identification tag of the amplified nucleic acid, thereby detecting the corresponding compound in the sample. This method may be carried out using any of the preferred embodiments described herein.

In a related aspect, the invention features a kit for compound detection, the kit including: (a) a nucleic acid-protein fusion, wherein the protein portion of the fusion specifically binds the compound and the nucleic acid portion of the fusion encodes the protein portion and includes a unique identification tag and in one embodiment, encodes the protein; (b) a PCR primer pair, wherein the first of the primers hybridizes to the nucleic acid portion of the fusion 5' to the unique identification tag and the second of the primers hybridizes to the nucleic acid portion of the fusion 3' to the unique identification tag and hybridization of the primers to the nucleic acid fusion permits amplification of the unique identification tag; and (c) a solid support including a nucleic acid which can hybridize to the unique identification tag.

In preferred embodiments, the kit further includes Taq polymerase; the nucleic acid-protein fusion is an RNA-protein fusion; the nucleic acid-protein fusion is covalently linked; the nucleic acid-protein fusion is covalently linked through a peptide acceptor; the peptide acceptor is puromycin; the nucleic acid-protein fusion does not bind the compound through a compound-specific antibody domain; the nucleic acid-protein fusion includes a scaffold domain; the nucleic acid-protein fusion includes a fibronectin scaffold domain; the fibronectin scaffold domain is the 10$^{th}$ domain of fibronectin type III; the nucleic acid-protein fusion includes an antibody scaffold domain; the nucleic acid-protein fusion binds the compound with an equilibrium constant of less than about 500 nM; the solid support includes an ordered array of single-stranded nucleic acids on its surface, each of the single-stranded nucleic acids being capable of hybridizing to a different unique identification tag; the solid support is a chip; the immobilized nucleic acid are DNAs, preferably configured as a DNA array; the compound is a protein; the kit includes at least 5 different nucleic acid-protein fusions, each specifically binding to a different compound; the kit includes at least 100 different nucleic acid-protein fusions, each specifically binding to a different compound; the kit includes at least 40,000 different nucleic acid-protein fusions, each specifically binding to a different compound; and/or the kit includes at least 500,000 different nucleic acid-protein fusions, each specifically binding to a different compound.

DETAILED DESCRIPTION

According to the multiplex diagnostic approach described herein, one begins with a set of uniquely defined high affinity binding reagents (typically protein binding reagents). Each of these reagents binds to a different target in a sample, facilitating the detection of several targets simultaneously. The targets of the binding reagents are frequently proteins, but they may be any moiety capable of specific binding, including, for example, nucleic acids or sugar moieties. Such binding reagents may represent naturally-occurring molecules or partially or completely synthetic amino acid sequences. Examples of naturally-occurring binding reagents include, without limitation, members of the following binding pairs: antigen/antibody pairs, protein/inhibitor pairs, receptor/ligand pairs (for example cell surface receptor/ligand pairs, such as hormone receptor/peptide hormone pairs), enzyme/substrate pairs (for example, kinase/substrate pairs), lectin/carbohydrate pairs, oligomeric or heterooligomeric protein aggregates, DNA binding protein/DNA binding site pairs, RNA/protein pairs, and nucleic acid duplexes, heteroduplexes, or ligated strands, as well as any molecule which is capable of forming one or more covalent or non-covalent bonds (for example, disulfide bonds) with any portion of a nucleic acid-protein fusion. In addition to naturally-occurring binding partner members, binding reagents may be derived by any technique, for example, by directed evolution approaches using a desired protein as the binding target.

Whether naturally-occurring or synthetic, when mixtures of protein binding reagents are utilized in a single diagnostic reaction mixture, they are preferably similar in composition and amino acid length. In a particularly preferred approach, one starts with a common amino acid scaffold or structural motif that displays the binding domain on one face of the molecule, as is the case for an antibody scaffold that displays CDR regions as a binding region of the molecule. In an alternative embodiment, the binding reagents do not bind target compounds through compound-specific antibody domains. A particularly useful binding scaffold is the $10^{th}$ domain of type III fibronectin which acts like an antibody mimic (see, for example, Lipovsek et al., Protein Scaffolds for Antibody Mimics and Other Binding Proteins, U.S. Ser. No. 09/456,693 now abandoned; U.S. Ser. No. 09/515,260 issued as U.S. Pat. No. 6,818,418; U.S. Ser. No. 09/688,566 now abandoned; WO 00/34784).

The compound to be detected by the present approach may be any substance to which a protein may bind, and is preferably itself a protein. Such target compounds may be present in any sample, for example, any biological sample. Typical biological samples include, without limitation, any fluid or tissue derived from an organism, for example, a plant or a mammal such as a human.

As a central feature of one embodiment of the invention, each of the binding domains is covalently attached to a nucleic acid that encodes the binding domain. Such nucleic acid-protein fusion molecules can be produced by any method, for example, by the method of Roberts and Szostak (Szostak et al., U.S. Ser. No. 09/007,005, now U.S. Pat. No. 6,258,558 B1, and U.S. Ser. No. 09/247,190, now U.S. Pat. No. 6,261,804 B1; Szostak et al., WO 98/31700; Roberts & Szostak, Proc. Natl. Acad. Sci. USA (1997) vol. 94, p. 12297–12302) using a peptide acceptor, such as puromycin, as a covalent linking agent. As used herein, by a "peptide acceptor" is meant any molecule capable of being added to the C-terminus of a growing protein chain by the catalytic activity of the ribosomal peptidyl transferase function. Typically, such molecules contain (i) a nucleotide or nucleotide-like moiety (for example, adenosine or an adenosine analog (di-methylation at the N-6 amino position is acceptable)), (ii) an amino acid or amino acid-like moiety (for example, any of the 20 D- or L-amino acids or any amino acid analog thereof (for example, O-methyl tyrosine or any of the analogs described by Ellman et al., Meth. Enzymol. 202: 301, 1991), and (iii) a linkage between the two (for example, an ester, amide, or ketone linkage at the 3' position or, less preferably, the 2' position); preferably, this linkage does not significantly perturb the pucker of the ring from the natural ribonucleotide conformation. Peptide acceptors may also possess a nucleophile, which may be, without limitation, an amino group, a hydroxyl group, or a sulfhydryl group. In addition, peptide acceptors may be composed of nucleotide mimetics, amino acid mimetics, or mimimetics of the combined nucleotide-amino acid structure. As noted above, puromycin represents a preferred peptide acceptor for use in the present method.

In an alternative embodiment, any other unique, PCR-amplifiable nucleic acid (for example, RNA, DNA, PNA, or any other nucleic acid which includes two or more covalently bonded, naturally-occurring or modified ribonucleotides or deoxyribonucleotides) can be coupled covalently or non-covalently to each individual binding domain. The protein portions of the fusions are typically composed of naturally-occurring amino acid residues, but may also include amino acid analogs or derivatives, joined by peptide or peptoid bond(s). The nucleic acid portion may or may not encode the coupled protein portion.

Of particular importance is that each binding domain is associated with (and can therefore be identified by) a unique, amplifiable nucleic acid tag, and that each tag in a multiplex reaction is of identical (or essentially identical) length to avoid amplification (for example, PCR) biases. Such unique identification tags are nucleic acid sequences that differ sufficiently in sequence from other tags in a given population or reaction mixture that significant cross-hybridization does not occur under the conditions employed.

These unique identification tags may be present in the protein encoding portion of the fusion (for example, the tag can be a randomized portion of the protein scaffold, such as a randomized loop of the $10^{th}$ domain of fibronectin type III). Alternatively, the unique identification tag can be added to the nucleic acid portion of the fusion molecule and can, for example, be positioned outside of a nucleic acid sequence which encodes a compound binding domain or, if present, its associated scaffold region. In the alternative embodiment, unique identification tags may be chosen which most effectively, most selectively, or most conveniently identify the fusion molecule. For example, if binding reagents are deconvoluted on a DNA chip, tag(s) may be chosen which best hybridize to immobilized chip nucleic acid(s) or which are compatible with commercially available chip arrays. Although DNA chips represent a preferred solid support according to the invention, deconvolution may also be carried out on other solid substrates including, without limitation, any other type of chip (for example, silica-based, glass, or gold chip), glass slide, membrane, bead, solid particle (for example, agarose, sepharose, or magnetic bead), column (or column material), membrane (for example, the membrane of a liposome or vesicle), test tube, or microtiter dish.

Using the affinity binding reagents described above, the present method may be carried out, in one preferred embodiment, as follows. The high affinity binding reagents, each containing a unique affinity binding domain and being present in a mixture of anywhere from 1 to 500,000 (each with equilibrium constants of less than 500 nM), are combined with a sample (for example, a biological sample), under conditions which allow each affinity binding domain to reproducibly recognize a binding partner(s). Following complex formation of the binding reagent with its binding partner, the complex is captured. This can be accomplished through any standard procedure, for example, by biotinylation of the biological sample, followed by capture of biotinylated complexes using immobilized streptavidin (for example, streptavidin immobilized on magnetic beads or a column). Alternatively, the initial protein sample may be preabsorbed onto a membrane and the binding domains mixed with the membrane. Complexes remain bound, while unbound binding reagents are washed away.

Following capture of bound complexes, binding domains that have bound their target(s) in the biological sample are detected simply by performing a PCR reaction using primers which hybridize to the nucleic acid portion of the fusion molecule. The PCR reaction uses primers pairs in which one primer binds 5' to the unique identification tag and the other primer binds 3' to the unique identification tag. Each of the unique identification tags is of essentially identical length to avoid PCR amplification bias. Preferably, the PCR reaction is carried out using standard quantitative methods (for example, using TAQMAN, Roche, distributed by Perkin Elmer).

If multiple complexes are isolated, the isolated pool is then deconvoluted and individual members identified. The identification step may be accomplished through direct sequencing. Alternatively, in a preferred feature of the invention, the isolated pool is deconvoluted and bound analytes identified using DNA chip array detection. In one preferred method, the PCR reaction is stopped following predefined cycles, and aliquots extracted. In this way, DNA array detection is performed on each aliquot, allowing for quantitative analysis of amounts of each species present in the pool. Again, a critical feature of the PCR step is that the unique identifiable tag is amplified, and that each amplified segment is the result of using identical primers that generate a DNA product of identical (or essentially identical) size.

In addition, the present invention includes kits for carrying out any of the methods described herein. Typically, these kits include at least three important components: (a) a nucleic acid-protein fusion having a protein portion that specifically binds to a desired compound and a nucleic acid portion that includes a unique identification tag and may, if desired, encode the protein portion; (b) a PCR primer pair, in which the first primer is designed to hybridize to the nucleic acid portion of the fusion 5' to the unique identification tag and the second primer is designed to hybridize to the nucleic acid portion of the fusion 3' to the unique identification tag and in which hybridization of the primers to the fusion permits amplification of the unique identification tag; and (c) a solid support that includes a nucleic acid that can hybridize to the unique identification tag In preferred embodiments, the kits of the invention may include any of the preferred components discussed above with respect to the preferred methods of the invention.

Use

The reagents of the present invention have a multitude of uses in the diagnostic industry and may be substituted for monoclonal antibodies in any use or method for which such antibodies are employed. In addition, the molecules described herein may be used for deconvoluting species in complex biological samples. In addition, the present approach offers a fast, simple way for detecting species using PCR, a detection technique that is virtually unparalleled in its sensitivity. Coupled with the unique advances for PCR in quantitation of individual species and in DNA array platforms for deconvoluting and detecting low levels of species, the present invention represents the state of the art in the diagnostic area.

OTHER EMBODIMENTS

Other embodiments are within the claims.

All publications mentioned in this specification are hereby incorporated by reference to the same extent as if each independent publication or patent application was specifically and individually indicated to be incorporated by reference.

What is claimed is:

1. A method for detecting multiple different compounds in a sample, said method comprising:
   (a) providing both a sample containing different compounds and a mixture of binding reagents, said binding reagents comprising nucleic acid-protein fusions, each fusion comprising (i) a protein portion which is known to specifically bind to one of said compounds and (ii) a nucleic acid portion which includes a unique identification tag;
   (b) contacting said sample with said binding reagents under conditions allowing said protein portions of said binding reagents and said compounds to form binding reagent-compound complexes;
   (c) capturing said binding reagent-compound complexes;
   (d) amplifying said unique identification tag included on said nucleic acid portions of said binding reagent-compound complexes; and
   (e) detecting said unique identification tag of each of said binding reagent-compound complexes, thereby detecting the corresponding compounds in said sample.

2. The method of claim 1, wherein said sample is a biological sample.

3. The method of claim 1, wherein said nucleic acid-protein fusion is an RNA-protein fusion.

4. The method of claim 1, wherein said nucleic acid-protein fusion is covalently linked through a peptide acceptor.

5. The method of claim 4, wherein said peptide acceptor is puromycin.

6. The method of claim 1, wherein said binding reagents do not bind said compounds through compound-specific antibody domains.

7. The method of claim 1, wherein each of said binding reagents comprises a scaffold domain.

8. The method of claim 7, wherein each of said binding reagents comprises a fibronectin scaffold domain.

9. The method of claim 8, wherein said fibronectin scaffold domain is the $10^{th}$ domain of fibronectin type III.

10. The method of claim 7, wherein each of said binding reagents comprises an antibody scaffold domain.

11. The method of claim 1, wherein said binding reagents bind said compounds with equilibrium constants of less than about 500 nM.

12. The method of claim 1, wherein said unique identification tags are detected using a solid support to which are immobilized nucleic acids specific for said unique identification tags and said detection is accomplished by hybridization of said unique identification tags to said immobilized nucleic acids.

13. The method of claim 12, wherein said solid support is a microchip.

14. The method of claim 12, wherein said immobilized nucleic acids are immobilized DNAs.

15. The method of claim 12, wherein said immobolized nucleic acids are presented in an array.

16. The method of claim 15, wherein said array is a DNA array.

17. The method of claim 1, wherein said amplifying step (d) is carried out using quantitative PCR.

18. The method of claim 1, wherein said compounds are proteins.

19. The method of claim 1, wherein said mixture of binding reagents comprises at least 5 different nucleic acid-protein fusions, each specifically binding to a different compound.

20. The method of claim 19, wherein said mixture of binding reagents comprises at least 100 different nucleic acid-protein fusions, each specifically binding to a different compound.

21. The method of claim 20, wherein said mixture of binding reagents comprises at least 40,000 different nucleic acid-protein fusions, each specifically binding to a different compound.

22. The method of claim 21, wherein said mixture of binding reagents comprises at least 500,000 different nucleic acid-protein fusions, each specifically binding to a different compound.

23. A kit for compound detection, said kit comprising:
(a) a nucleic acid-protein fusion, wherein the protein portion of said fusion specifically binds said compound and the nucleic acid portion of said fusion includes a unique identification tag;
(b) a PCR primer pair, wherein the first primer hybridizes to said nucleic acid portion of said fusion 5' to said unique identification tag and the second primer hybridizes to said nucleic acid portion of said fusion 3' to said unique identification tag and hybridization of said first and second primers to said nucleic acid portion permits amplification of said unique identification tag; and
(c) a solid support comprising a nucleic acid which can hybridize to said unique identification tag.

24. The kit of claim 23, wherein said kit further comprises Taq polymerase.

25. The kit of claim 23, wherein said nucleic acid-protein fusion is an RNA-protein fusion.

26. The kit of claim 23, wherein said nucleic acid-protein fusion is covalently linked through a peptide acceptor.

27. The kit of claim 26, wherein said peptide acceptor is puromycin.

28. The kit of claim 23, wherein said nucleic acid-protein fusion does not bind said compound through a compound-specific antibody domain.

29. The kit of claim 23, wherein said nucleic acid-protein fusion comprises a scaffold domain.

30. The kit of claim 29, wherein said nucleic acid-protein fusion comprises a fibronectin scaffold domain.

31. The kit of claim 30, wherein said fibronectin scaffold domain is the $10^{th}$ domain of fibronectin type III.

32. The kit of claim 29, wherein said nucleic acid-protein fusion comprises an antibody scaffold domain.

33. The kit of claim 23, wherein said nucleic acid-protein fusion binds said compound with an equilibrium constant of less than about 500 nM.

34. The kit of claim 23, wherein said solid support is a chip.

35. The kit of claim 23, wherein said solid support comprises an ordered array of single-stranded nucleic acids on its surface, each of said single-stranded nucleic acids being capable of hybridizing to a different said unique identification tag.

36. The kit of claim 35, wherein said solid support is a microchip.

37. The kit of claim 35, wherein said immobilized nucleic acids are immobilized DNAs.

38. The kit of claim 35, wherein said immobolized nucleic acids are presented in an array.

39. The kit of claim 38, wherein said array is a DNA array.

40. The kit of claim 23, wherein said compound is a protein.

41. The kit of claim 23, wherein said kit comprises at least 5 different nucleic acid-protein fusions, each different nucleic acid-protein fusion characterized as being capable of specific binding to a different compound.

42. The kit of claim 41, wherein said kit comprises at least 100 different nucleic acid-protein fusions, each different nucleic acid-protein fusion characterized as being capable of specific binding to a different compound.

43. The kit of claim 42, wherein said kit comprises at least 40,000 different nucleic acid-protein fusions, each different nucleic acid-protein fusion characterized as being capable of specific binding to a different compound.

44. The kit of claim 43, wherein said kit comprises at least 500,000 different nucleic acid-protein fusions, each different nucleic acid-protein fusion characterized as being capable of specific binding to a different compound.

* * * * *

UNITED STATES PATENT AND TRADEMARK OFFICE
CERTIFICATE OF CORRECTION

| | |
|---|---|
| PATENT NO. | : 7,022,479 B2 |
| APPLICATION NO. | : 10/212620 |
| DATED | : April 4, 2006 |
| INVENTOR(S) | : Richard W. Wagner |

It is certified that error appears in the above-identified patent and that said Letters Patent is hereby corrected as shown below:

In Claim 38, Column 8, line 29, please correct "immobolized" to read --immobilized--.

Signed and Sealed this

Eleventh Day of July, 2006

JON W. DUDAS
*Director of the United States Patent and Trademark Office*